(12) United States Patent
Zou et al.

(10) Patent No.: US 10,675,470 B2
(45) Date of Patent: Jun. 9, 2020

(54) SYSTEMS AND METHODS FOR ACTIVE CHARGE-BALANCING FOR HIGH-FREQUENCY NEURAL STIMULATION

(71) Applicant: Verily Life Sciences LLC, South San Francisco, CA (US)

(72) Inventors: You Zou, Redwood City, CA (US); Peng Cong, Burlingame, CA (US); Ganesh Balachandran, Mountain View, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days.

(21) Appl. No.: 15/810,781

(22) Filed: Nov. 13, 2017

(65) Prior Publication Data
US 2018/0133482 A1    May 17, 2018

Related U.S. Application Data

(60) Provisional application No. 62/421,561, filed on Nov. 14, 2016.

(51) Int. Cl.
*A61N 1/00* (2006.01)
*A61N 1/36* (2006.01)
(Continued)

(52) U.S. Cl.
CPC ......... *A61N 1/36157* (2013.01); *A61N 1/025* (2013.01); *A61N 1/0551* (2013.01);
(Continued)

(58) Field of Classification Search
CPC .............. A61N 1/36157; A61N 1/3716; A61N 1/36167; A61N 1/36153; A61N 1/36142;
(Continued)

(56) References Cited

U.S. PATENT DOCUMENTS

| | | | | |
|---|---|---|---|---|
| 4,055,189 A | * | 10/1977 | Auerbach | ............ A61H 31/006 607/12 |
| 8,478,420 B2 | | 7/2013 | Armstrong et al. | |

(Continued)

FOREIGN PATENT DOCUMENTS

CN            204840670           12/2015

OTHER PUBLICATIONS

International Application No. PCT/US2017/061340, "PCT Search Report", dated Feb. 16, 2018, 14 pages.
(Continued)

*Primary Examiner* — Scott M. Getzow
(74) *Attorney, Agent, or Firm* — Kilpatrick Townsend & Stockton LLP (57) ABSTRACT

Systems and methods for active charge-balancing for high frequency neural stimulation are disclosed. One illustrative method described herein includes: applying, through a pair of electrodes electrically coupled to a bundle of nerve fibers during a stimulation phase of a neural stimulation procedure, a first current to the bundle of nerve fibers; applying, through the pair of electrodes during a recovery phase of the neural stimulation procedure, a second current to the bundle of nerve fibers, the first current and the second current having opposite polarities; determining sampled voltages between the pair of electrodes during the stimulation phase, during the recovery phase, or between the stimulation phase and the recovery phase; determining a charge buildup in the bundle of nerve fibers based on the sampled voltages; applying, through the pair of electrodes during the stimulation phase or during the recovery phase, a delta current to the bundle of nerves based on the sampled voltages to minimize the charge build up.

16 Claims, 4 Drawing Sheets

(51) Int. Cl.
*A61N 1/05* (2006.01)
*A61N 1/02* (2006.01)
*A61N 1/06* (2006.01)

(52) U.S. Cl.
CPC ........... *A61N 1/06* (2013.01); *A61N 1/36053* (2013.01); *A61N 1/36125* (2013.01); *A61N 1/36142* (2013.01); *A61N 1/36153* (2013.01); *A61N 1/36167* (2013.01); *A61N 1/36171* (2013.01)

(58) Field of Classification Search
CPC ...... A61N 1/36053; A61N 1/06; A61N 1/025; A61N 1/36171; A61N 1/36125; A61N 1/0551
See application file for complete search history.

(56) References Cited

U.S. PATENT DOCUMENTS

| | | | |
|---|---|---|---|
| 2008/0015641 A1* | 1/2008 | Armstrong | A61N 1/08 607/2 |
| 2009/0062880 A1* | 3/2009 | Li | A61N 1/025 607/32 |
| 2010/0324630 A1 | 12/2010 | Lee et al. | |
| 2011/0077698 A1* | 3/2011 | Tsampazis | A61N 1/08 607/2 |
| 2012/0259382 A1 | 10/2012 | Trier et al. | |
| 2013/0096643 A1* | 4/2013 | Fang | A61N 1/36071 607/46 |
| 2013/0204319 A1* | 8/2013 | Trier | A61N 1/36071 607/46 |
| 2013/0310894 A1 | 11/2013 | Trier | |
| 2014/0277260 A1* | 9/2014 | Khalil | A61N 1/37241 607/46 |
| 2016/0038739 A1* | 2/2016 | Liu | A61N 1/3787 607/45 |

OTHER PUBLICATIONS

International Application No. PCT/US2017/061340 , "International Preliminary Report on Patentability", dated May 23, 2019, 9 pages.

* cited by examiner

SYSTEMS AND METHODS FOR ACTIVE CHARGE-BALANCING FOR HIGH-FREQUENCY NEURAL STIMULATION

CROSS-REFERENCE TO RELATED APPLICATIONS

The present application claims priority to Provisional Application No. 62/421,561, filed on Nov. 14, 2016, and entitled "Active Charge-Balancing Circuitry for High-Frequency Neural Stimulation," the entirety of which is hereby incorporated by reference herein.

FIELD OF THE INVENTION

The present invention relates to control circuits for neural stimulation devices, in particular circuits for active charge-balancing for high frequency neural stimulation.

BACKGROUND

Peripheral Nerve Stimulation ("PNS") therapies, such as Vagus Nerve Stimulation ("VNS"), are promising treatments for many chronic diseases including epilepsy and depression. Traditional stimulation frequency is in the range of a few tens of hertz to a few hundreds of hertz. Higher stimulation frequency in kHz range, e.g. from 1 kHz to 50 kHz, may benefit for some diseases. Safety is one of the most important consideration for neuromodulation, thus there is a need for systems and methods for active charge balancing.

SUMMARY

One illustrative method described herein includes: applying, through a pair of electrodes electrically coupled to a bundle of nerve fibers during a stimulation phase of a neural stimulation procedure, a first current to the bundle of nerve fibers; applying, through the pair of electrodes during a recovery phase of the neural stimulation procedure, a second current to the bundle of nerve fibers, the first current and the second current having opposite polarities; determining sampled voltages between the pair of electrodes during the stimulation phase, during the recovery phase, or between the stimulation phase and the recovery phase; determining a charge buildup in the bundle of nerve fibers based on the sampled voltages; applying, through the pair of electrodes during the stimulation phase or during the recovery phase, a delta current to the bundle of nerves based on the sampled voltages to minimize the charge build up.

Another illustrative embodiment of the present disclosure comprises a neural stimulation apparatus. An illustrative system described herein comprises: a circuit configured to: apply, through a pair of electrodes electrically coupled to a bundle of nerve fibers during a stimulation phase of a neural stimulation procedure, a first current to the bundle of nerve fibers; apply, through the pair of electrodes during a recovery phase of the neural stimulation procedure, a second current to the bundle of nerve fibers, the first current and the second current having opposite polarities; determine sampled voltages between the pair of electrodes during the stimulation phase, during the recovery phase, or between the stimulation phase and the recovery phase; determine a charge buildup in the bundle of nerve fibers based on the sampled voltages; apply, through the pair of electrodes during the stimulation phase or during the recovery phase, a delta current to the bundle of nerves based on the sampled voltages to minimize the charge build up.

Another illustrative system described herein comprises: a pair of electrodes configured to be coupled proximate to a bundle of nerve fibers; a stimulation circuit electrically coupled to the pair of electrodes and including a first current source for applying a first current and a second current to the bundle of nerve fibers through the pair of electrodes during a neural stimulation procedure, the second current having an opposing polarity to the first current; and a balancing circuit coupled to a switch of the stimulation circuitry for activating a second current source to apply a delta current to the bundle of nerve fibers through the pair of electrodes concurrently with the first current or the second current depending on a voltage differential between the pair of electrodes.

These illustrative embodiments are mentioned not to limit or define the limits of the present subject matter, but to provide examples to aid understanding thereof. Illustrative embodiments are discussed in the Detailed Description, and further description is provided there. Advantages offered by various embodiments may be further understood by examining this specification and/or by practicing one or more embodiments of the claimed subject matter.

BRIEF DESCRIPTION OF THE DRAWINGS

A full and enabling disclosure is set forth more particularly in the remainder of the specification. The specification makes reference to the following appended figures.

DETAILED DESCRIPTION

Reference will now be made in detail to various and alternative illustrative embodiments and to the accompanying drawings. Each example is provided by way of explanation, and not as a limitation. It will be apparent to those skilled in the art that modifications and variations can be made. For instance, features illustrated or described as part of one embodiment may be used in another embodiment to yield a still further embodiment. Thus, it is intended that this disclosure include modifications and variations as come within the scope of the appended claims and their equivalents.

Illustrative Example of Active Charge-Balancing for High-Frequency Neural Stimulation One illustrative embodiment of the present disclosure comprises a system for applying high-frequency neural stimulation to a subject. In the illustrative embodiment, such a system may comprise two or more electrodes coupled proximate to nerve fibers of a subject. In the illustrative embodiment, current is applied to the electrodes to stimulate the nerves.

In the illustrative embodiment, at least two currents may be applied to the subject, and these two currents may have opposite polarities. Further, in the illustrative embodiment, a sensing circuit may sample voltage values across the two electrodes at various times (e.g., during the stimulation phase, during the recovery phase, or between the stimulation phase and the recovery phase). The sensing circuit may determine a charge buildup in the nerve fibers based on the voltage values across the two electrodes. Thus, a compensation circuit may apply a delta current to the nerve fibers. This delta current may be configured to minimize or compensate for the charge buildup.

Examples are described herein in the context of circuitry for neural stimulation. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Figure 1:
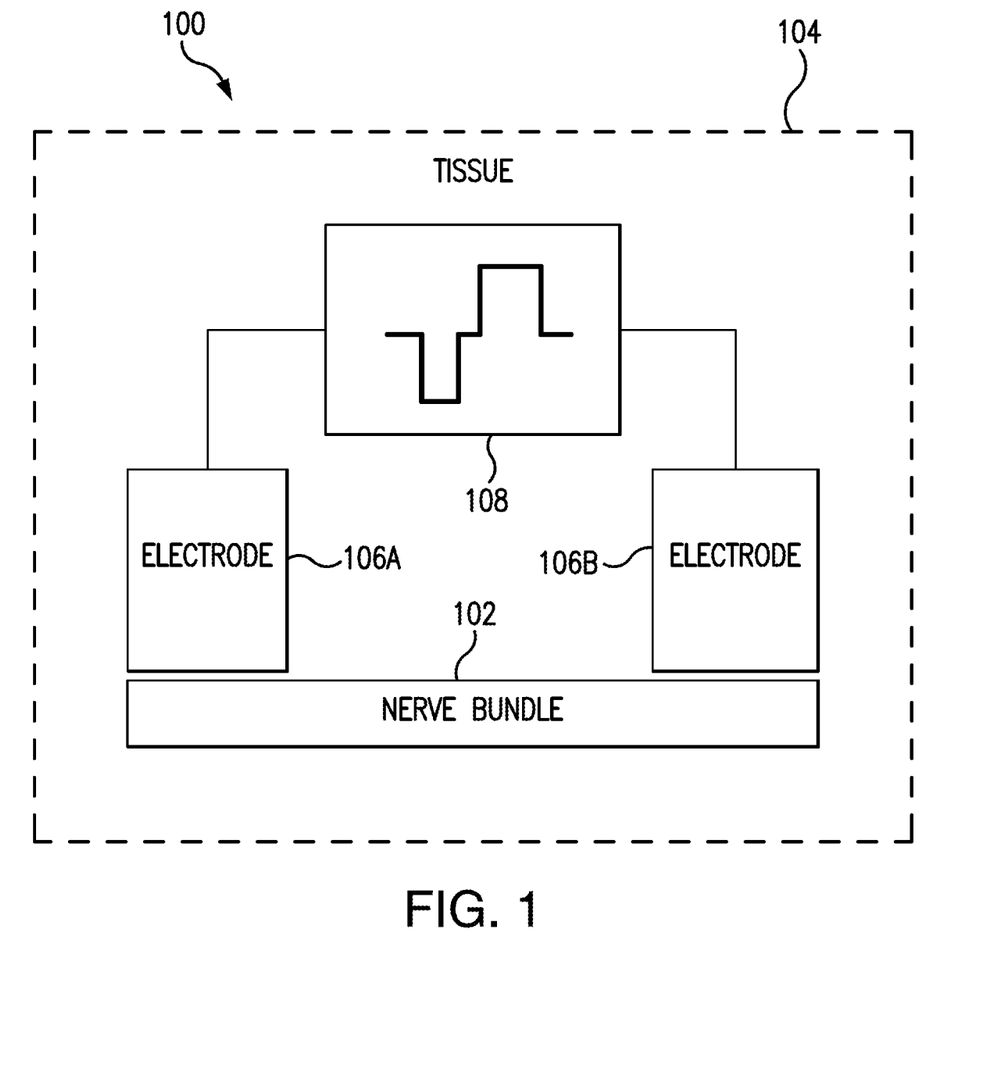
FIG. 1 shows an example embodiment of a neural stimulation apparatus according to some aspects of the present disclosure.

Illustrative Systems for Active Charge-Balancing for High-Frequency Neural Stimulation FIG. 1 shows an example of a neural stimulation apparatus 100 according to some aspects of the present disclosure. In one illustrative example, the neural stimulation apparatus 100 is used during a neural stimulation procedure, such as neuromodulation therapy, to treat a chronic disease. During neuromodulation therapy, electrical stimulation is delivered to a bundle of nerve fibers 102 within tissue 104 of a patient. The neural stimulation apparatus 100 includes a pair of electrodes 106A, 106B implanted into the patient's tissue 104 and positioned proximate to the bundle of nerve fibers 102. The electrodes 106A, 106B include internal circuitry to deliver current to stimulate to the bundle of nerve fibers 102.

A non-limiting example of the internal circuitry of the electrodes 106A, 106B includes a double-layer capacitor and two resistors. In one example arrangement of the internal circuitry, a resistor-capacitor ("RC") circuit is created by the double-layer capacitor positioned in parallel with a first resistor corresponding to the Faradaic impedance caused by the transfer of electrons from the electrodes to the bundle of nerve fibers 102. In some embodiments, the capacitor may have a value range between 100 nanoFarads and 1 microFarad. In some embodiments, the first resistor may have a value range between 100 kiloohms and 1 megaohm. The second resistor is positioned in series with the RC circuit and may correspond to electrolyte impedance (e.g., the impedance of the tissue 104). In some embodiments, the second resistor may have a value range between 500 ohms and 2 kiloohms. The electrodes include a conductive metal material, such as, but not limited to, copper, silver, or platinum.

The current delivered to the bundle of nerve fibers 102 through the electrodes 106A, 106B creates an electrical field that applies an electronic charge to the bundle of nerve fibers 102. The current delivered through the electrodes 106A, 106B is generated by stimulation circuitry 108 positioned between the electrodes 106A, 106B. The stimulation circuitry 108 may cause current to flow in a path that creates a chemical reaction, leaving a positive charge on the bundle of nerve fibers 102. The phase of a neural stimulation procedure corresponding to creating the chemical reaction is referred to as the stimulation phase. The stimulation circuitry 108 may also deliver a second current to the bundle of nerve fibers 102 to reverse the chemical reaction on the bundle of nerve fibers 102. This phase of the neural stimulation procedure is referred to as the recovery phase. During the recovery phase, the charge remaining on the bundle of nerve fibers 102 is minimized or removed. The current used during the recovery phase and the current used during the stimulation phase have opposing polarities to minimize the charge and allow the bundle of nerve fibers to recover. A buildup of a charge on the bundle of nerve fibers 102 may cause damage to the nerves and, in some instances, also damage the electrodes 106A, 106B.

In some aspects, the neural stimulation apparatus 100 is configured to operate in both a low-frequency range and a high-frequency range. The low-frequency range may include frequencies between approximately 10 hertz and 1 kilohertz. The high-frequency range may include frequencies between approximately 1 kilohertz and 50 kilohertz. In some aspects, the neural stimulation apparatus 100 may be tunable to a high-frequency or low-frequency range depending on the chronic disease being treated through the neural stimulation process.

During operation of the neural stimulation apparatus 100, the opposing polarities of the currents applied to the bundle of nerve fibers 102 may not eliminate all of the charge, leaving residual charge on the bundle of nerve fibers 102. During low-frequency operation, the time between stimulation phases may allow an opportunity for the residual charge to dissipate naturally. In some configurations of the neural stimulation apparatus 100, the electrodes 106A, 106B may be temporarily shorted to extend the opportunity for the residual charge to dissipate. But during high-frequency operation of the neural stimulation apparatus 100, the limited time between stimulation phases does not provide enough time for natural dissipation of the residual charge. Also, a high constant of the RC circuit of the electrodes 106A, 106B renders infeasible shorting the electrodes 106A, 106B. To prevent the buildup of the residual charge during high-frequency operation, the stimulation circuitry 108 includes a balancing circuit that generates a delta current that is applied to the bundle of nerve fibers 102 during the stimulation stage or the recovery stage, depending on the voltage differential between the electrodes 106A, 106B. The delta current may minimize or remove the residual charge from the bundle of nerve fibers 102 to prevent a buildup that can damage the bundle of nerve fibers 102 or the electrodes 106A, 106B.

Figure 2:
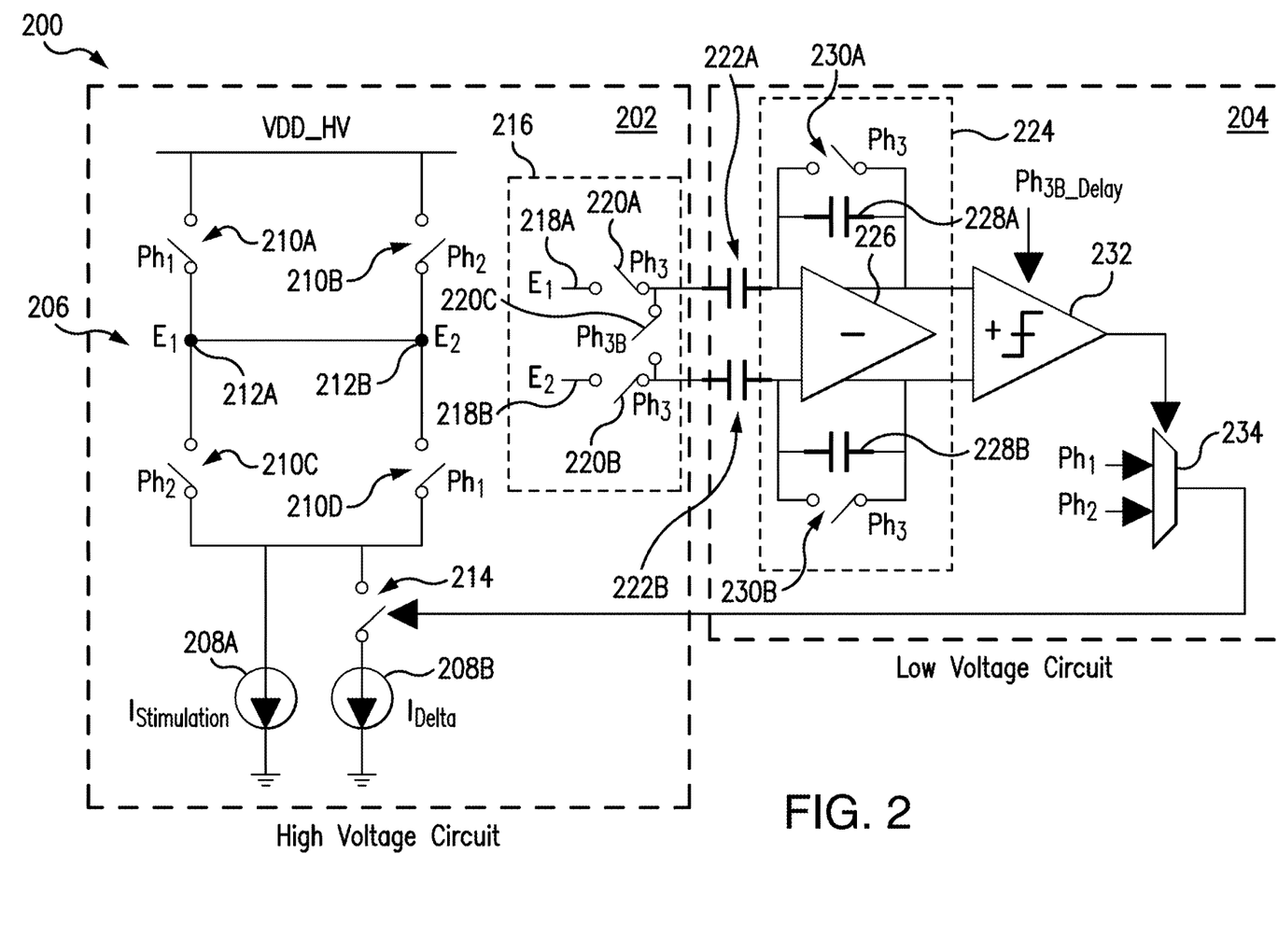
FIG. 2 shows an example embodiment of stimulation circuitry for applying a delta current during high-frequency operation of a neural stimulation apparatus according to aspects of the present disclosure.

FIG. 2 shows an example of stimulation circuitry 200 for applying a delta current during high-frequency operation of a neural stimulation apparatus according to aspects of the present disclosure. In some aspects, the stimulation circuitry 200 may represent the stimulation circuitry 108 of the neural stimulation apparatus 100 of FIG. 1. The stimulation circuitry 200 includes neuromodulation circuitry 202 and balancing circuitry 204.

The neuromodulation circuit 202 includes an H-bridge circuit 206 and current sources 208A, 208B. In some aspects, the H-bridge circuit 206 is positioned between the electrodes 106A, 106B of FIG. 1. The H-bridge circuit 206 includes switches 210A-210D defining flow paths between the electrodes 106A, 106B for the currents used during the stimulation and recovery phases of the neural stimulation process. The switches 210A-210D are configured to operate (e.g., open and close) in response to an application of a voltage $Ph_1$ or $Ph_2$ to the switches 210A-210D from one or more control devices (not shown). For example, the switches 210A, 210D respond to an application of voltage $Ph_1$ and the switches 210B, 210C respond to an application of voltage $Ph_2$. Accordingly, the switches 210A, 210D may actuate in concert between an open position and a closed position. The switches 210B, 210C may actuate in concert between an open position and a closed position separate from the switches 210A, 210D.

In one example, the voltages $Ph_1$ or $Ph_2$ may be applied such that the switches 210A, 210D are in an open position when the switches 210B, 210C are in a closed position and the switches 210A, 210D are in a closed position when the switches 210B, 210C are in an open position. The alternating positioning of the switches 210A-210D defines two current paths between the electrodes 106A, 106B of FIG. 1. For example, when the switches 210A, 210D are in a closed position and the switches 210B, 210C are in an open position, a first current path may have an "S" shape extending from the voltage source VDD_HV, through the switch 210A in a closed position, node 212A, node 212B, switch 210D in a closed position, and to the ground source through the current source 208A. When the switches 210B, 210C are in a closed position and 210A, 210D are in an open position, a second current path may have a "reverse-S" shape extending from the voltage source VDD_HV, through the switch 210B in a closed position, node 212B, node 212A, switch 210C in a closed position, and to the ground source through the current source 208. The switches' 210A-210D actuation corresponds to the phase of the neural stimulation process. For example, a neural stimulation apparatus may operate in a stimulation phase when the switches 210A, 210D are in a closed position and the switches 210B, 210C are in an open position. The apparatus may operate in the recovery phase when the switches 210B, 210C are in a closed position and 210A, 210D are in an open position. After each cycle of the stimulation phase and the recovery phase, all of the switches 210A-210D may return to an open position to complete a stimulation cycle The current source 208A is positioned in both flow paths defined by the switches 210A-210D. The current flow through the current flow paths defined by the switches 210A-210D determines the polarity of the current generated by the current source 208A. In some aspects, the current source 208A is an independent current source that applies a stimulation current, $I_{Stimulation}$, that is independent of the voltage across the current source 208A. The stimulation current is delivered to the bundle of nerve fibers 102 through the electrodes 106A, 106B.

The current source 208B is positioned in a flow path defined by the switches 210A-210D and an additional switch, switch 214. The switch 214 is actuated by an output of the balancing circuitry 204. The balancing circuitry 204 may output a voltage $Ph_1$ or $Ph_2$ to cause the switch 214 to actuate with one of the pair of switches 210A, 210D (e.g., where the balancing circuitry 204 outputs a voltage $Ph_1$) or the pair of switches 210B, 210C (e.g., where the balancing circuitry 204 outputs a voltage $Ph_2$). The switch 214 in a closed position defines an additional current flow path with one of the pair of switches 210A, 210D or the pair of switches 210B, 210C for a delta current, $I_{Delta}$, to be applied to the bundle of nerve fibers 102.

The balancing circuitry 204 operates using a sample of the voltages $E_1$, $E_2$ at nodes 212A, 212B, respectively, obtained by a sampling circuit 216. Although the balancing circuitry 204 is shown as included in the neuromodulation circuit 202, the balancing circuit may be included in the balancing circuitry and used to sample the voltages $E_1$, $E_2$ at nodes 212A, 212B within the neuromodulation circuit 202. The voltages $E_1$, $E_2$ correspond to the voltage across the electrodes 106A, 106B. The sampling circuit 216 includes couplers 218A, 218B and switches 220A-220C to selectively sample the voltages $E_1$, $E_2$. The couplers 218A, 218B may be coupled to the nodes 212A, 212B. The couplers 218A, 218B may obtain samples of the voltages $E_1$, $E_2$ when the switches 220A, 220B are in a closed position. The switches 220A, 220B are controlled by the control device (not shown) applying a voltage $Ph_3$ to the switches. The switch 220C is positioned in parallel with the couplers 218A, 218B to short or otherwise turn off the sampling circuit 216 and prevent further samples. In some aspects, the sampling circuit 216 is operable during a period between the stimulation and recovery phase. For example, the switches 220A, 220B may be in an open position during the stimulation phase and the voltage $Ph_3$ is applied to actuate the switches 220A, 220B to the closed position to obtain the sample voltages before the recovery phase. In other aspects, the sampling circuit 216 is operable during the stimulation or recovery phase or subsequent to a cycle of the stimulation and recovery phases. Once a sufficient sample is obtained, a voltage $Ph_{3B}$ may be applied to actuate the switch 220C to a closed position to stop the sampling process.

The sampling circuit 216 may route the samples to the capacitors 222A, 222B of the balancing circuitry 204. The capacitors 222A, 222B operate as storage devices to temporarily retain the samples and control the discharge of the samples to an amplifier circuit 224. The amplifier circuit 224 includes an amplifier 226, capacitors 228A, 228B, and switches 230A, 230B. The amplifier 226 includes two inputs and two outputs. The amplifier 226 may amplify the strength of each sample. The capacitors 228A, 228B and the switches 230A, 230B operate to complete the charge transfer from the capacitors 222A, 222B to amplify the voltage sampled by the capacitors 222A, 222B. The switches 230A, 230B are actuated by the same voltage $Ph_1$ that controls the switches 220A, 220B of the sampling circuit 216. The balancing circuit 216 in combination with the capacitors 222A, 222B and the amplifier circuit 224 together form a switched-capacitor amplifier.

The amplifier circuit 226 is coupled to a comparator 232. The comparator 232 includes two inputs that may receive the samples from the outputs of the amplifier 226. The comparator 232 may compare the samples and output a voltage signal that indicates which sample voltage is larger. In some aspects, the output voltage signal, $V_O$, corresponds to the following:

$$V_O = \begin{cases} 1, & \text{if } E_1 > E_2 \\ 0, & \text{if } E_2 < E_1 \end{cases}.$$

The comparator 232 includes a control input coupled to the control device (not shown) that applies a voltage $Ph_{3B\_Delay}$ to actuate the comparator 232. The voltage Ph$_{3B\_Delay}$ corresponds to the voltage Ph$_{3B}$ applied to the switch 220C of the sampling circuit 216, but applied at a predetermined time delay.

The comparator 232 is coupled to a multiplexer 234. The multiplexer 234 includes two inputs, a selector input, and a single output. The two inputs are coupled to the control devices for applying the voltages Ph$_1$ and Ph$_2$. The selector input is coupled to the comparator 232 to receive the output voltage signal V$_O$. The output of the multiplexer controls the switch 214, as discussed above. In some aspects, the output of the multiplexer, Z$_O$, corresponds to the following:

$$Z_O = \begin{cases} Ph_1, & \text{if } V_O = 0 \\ Ph_2, & \text{if } V_O = 1 \end{cases}.$$

Figure 3:
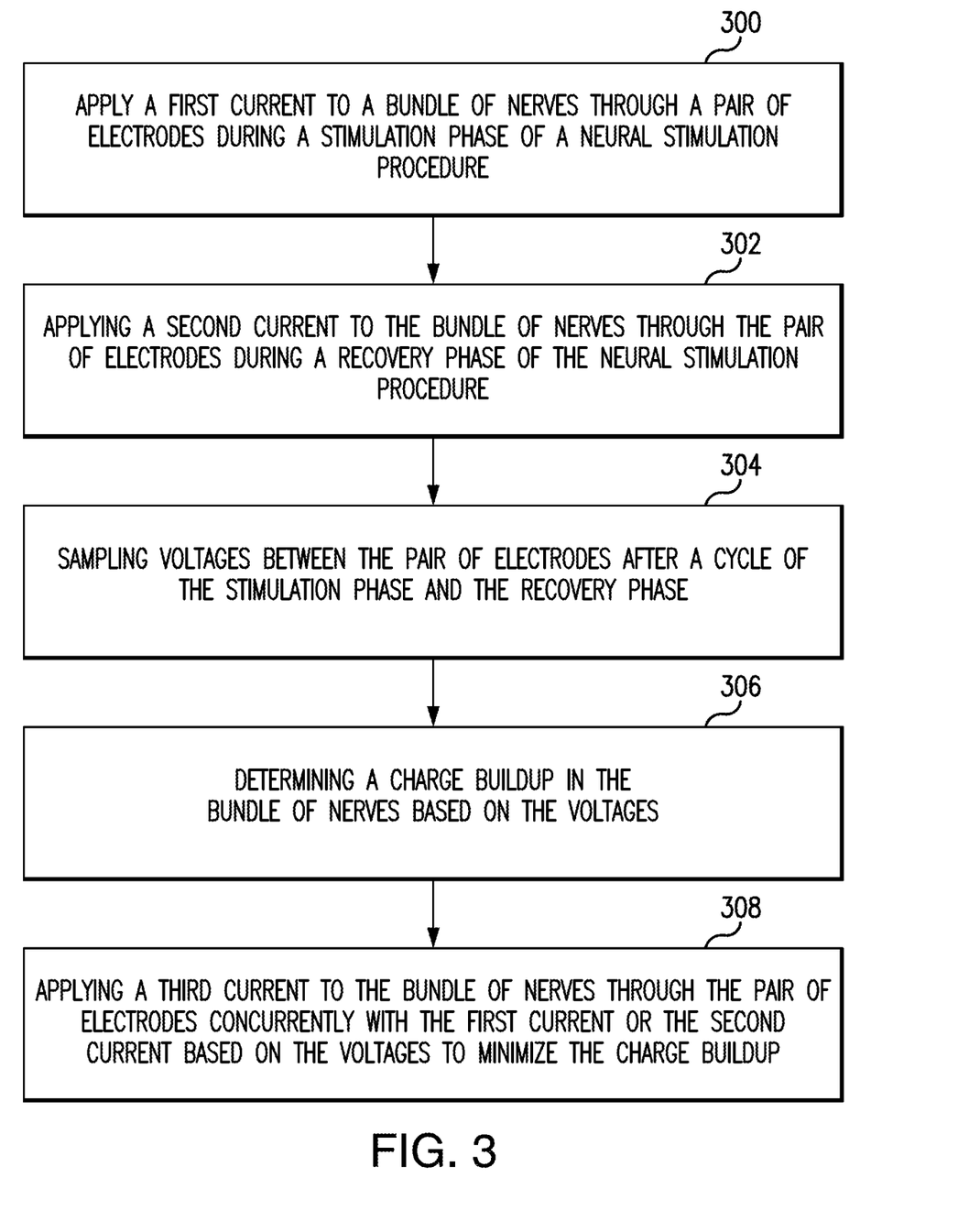
FIG. 3 is a flowchart of an example embodiment of a process for actively balancing charges during a neural stimulation process according to an aspect of the present disclosure.

FIG. 3 is a flowchart of an example of a process for actively balancing charges during a neural stimulation process according to an aspect of the present disclosure. The process is described with respect to the neural stimulation apparatus 100 of FIG. 1 and the stimulation circuitry 200 of FIG. 2.

In block 300, a current is applied to the bundle of nerve fibers 102 through the pair of electrodes 106A, 106B. The current is generated by the current source 208A and corresponds to the stimulation current applied to the bundle of nerve fibers 102 during the stimulation phase of the neural stimulation process. The current may be generated in response to the switches 210A, 210D actuating in response to the voltage Ph$_1$ to close the switches 210A, 210D during the stimulation phase. The switches 210A, 210D form the S-shaped flow path between the voltage source VDD_HV and the ground source through which the current may flow through the bundle of nerve fibers 102.

In block 302, a second current is applied to the bundle of nerve fibers 102 through the pair of electrodes 106A, 106B. The second current may have an opposing polarity to the first current of block 300. The current may be generated in response to the switches 210B, 210C actuating in response to the voltage Ph$_2$ to close the switches 210B, 210C. The second current may be applied during the recovery phase. The opposing polarity of the second current may reverse the chemical reactions to the bundle of nerve fibers 102 caused by the first current of block 300.

In block 304, voltages between the pair of electrodes 106A, 106B are sampled. In some aspects, the voltages are sampled at the nodes 212A, 212B. The voltages may be sampled by the sampling circuit 214 and routed to the balancing circuit 204 to determine a voltage for controlling the switch 212 and causing the current source 208B to generate the delta current. In some aspects, the voltages between the nodes 212A, 212B may be sampled between stimulation cycles (e.g., after each iteration of the stimulation phase and the recovery phase.

In block 306, a charge buildup in the bundle of nerve fibers 102 is determined. The charge buildup may occur naturally in response to stimulation cycles as the stimulation phase and the recovery phase do not create an ideal match in opposing currents to cancel all of the associated charges to the bundle of nerve fibers 102. In some aspects, the charge buildup is determined based on the voltage differential across the electrodes 106A, 106B. The sample of the voltages E$_1$ and E$_2$ are routed to a comparator for comparison to determine which voltage is greater. A charge buildup may include negative charges when and E$_2$ is greater than E$_1$ and positive charges when E$_1$ is greater than E$_2$.

In block 308, a third current is applied to the bundle of nerve fibers 102 through the pair of electrodes 106A, 106B. The third current corresponds to the delta current, Delta. In some aspects, the magnitude of the current corresponds to the voltage differential between the electrodes 106A, 106B. For example, the greater the difference between the voltages of the electrodes 106A, 106B, the stronger the current applied. In some aspects, the delta current will be applied to the bundle of nerve fibers 102 concurrently with the first current or the second current. The timing of the third signal's application is dependent on the voltage differential. For example, when E$_2$ is greater than E$_1$, the delta current may be applied during the stimulation phase (e.g., when the voltage Ph1 is applied to the switches 210A, 210D) to counteract the negative charge buildup. Similarly, when E$_1$ is greater than E$_2$, the delta current may be applied during the recovery phase (e.g., when the voltage Ph$_2$ is applied to the switches 210B, 210C) to counteract the positive charge buildup.

Figure 4:
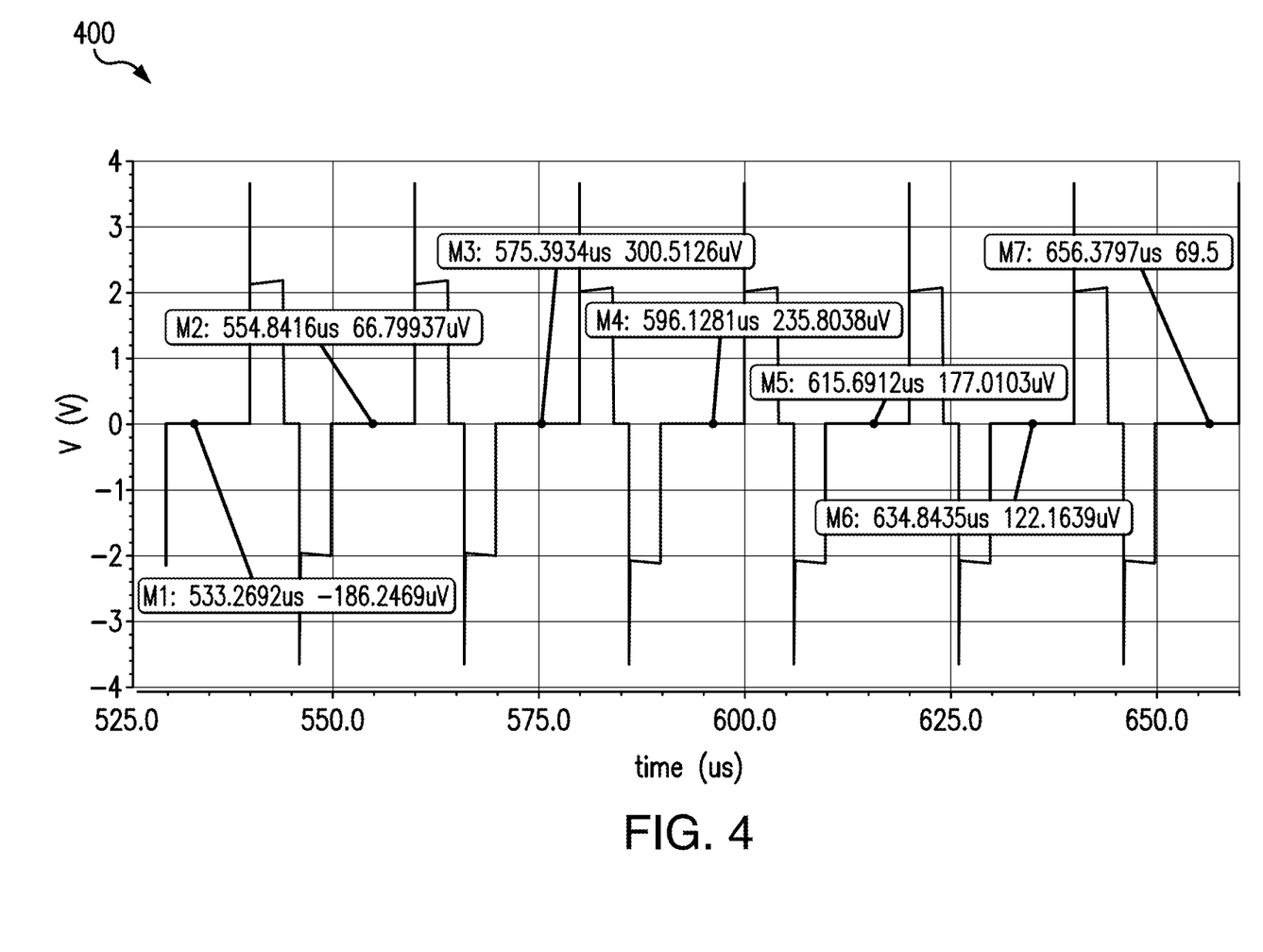
FIG. 4 is an example of a graph showing a simulated measurement of voltage differential between electrodes in a neural stimulation apparatus.

FIG. 4 is an example of a graph 400 simulating voltage differential measurements between the electrodes 106A, 106B in a neural stimulation apparatus including the balancing circuitry 204 according to aspects of the present disclosure. The measurements M1-M7 are taken after one or more stimulation cycles. The oscillation between positive and negative voltage differential values is due to the changes in polarities of the stimulation currents during the stimulation cycle. Regardless of the polarities, the graph 400 illustrates that the delta current may be triggered as the voltage differential moves away from a zero value. For example, at measurement M1, E$_2$ is greater than E$_1$ as indicated by the negative value. The delta current is applied during the stimulation phase to drive the voltage differential back toward zero. Similarly, at measurement M3, E$_1$ is greater than E$_2$ as indicated by the positive value. The delta current is applied during the recovery phase to drive the voltage differential back toward zero In some embodiments the stimulation current comprises 3.1 mA at a frequency of 50 KHz, with a pulse width of 4 microseconds, with a non-overlap time of 2 microseconds. In other embodiments different values may be applied, e.g., a current of 1 mA, a frequency of 41.66 KHz.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process that is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered. Accordingly, the above description does not bound the scope of the claims.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

Embodiments in accordance with aspects of the present subject matter can be implemented in digital electronic circuitry, in computer hardware, firmware, software, or in combinations of the preceding. In one embodiment, a computer may comprise a processor or processors. The processor comprises or has access to a computer-readable medium, such as a random access memory (RAM) coupled to the processor. The processor executes computer-executable program instructions stored in memory, such as executing one or more computer programs including a sensor sampling routine, selection routines, and other routines to perform the methods described above.

Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example tangible computer-readable media, that may store instructions that, when executed by the processor, can cause the processor to perform the steps described herein as carried out, or assisted, by a processor. Embodiments of computer-readable media may comprise, but are not limited to, all electronic, optical, magnetic, or other storage devices capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. Also, various other devices may include computer-readable media, such as a router, private or public network, or other transmission device. The processor, and the processing, described may be in one or more structures, and may be dispersed through one or more structures. The processor may comprise code for carrying out one or more of the methods (or parts of methods) described herein.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art.

What is claimed:

1. A method for actively balancing charges for a high-frequency neural stimulation device, the method comprising:
    applying, through a pair of electrodes electrically coupled to a bundle of nerve fibers during a stimulation phase of a neural stimulation procedure, a first current to the bundle of nerve fibers;
    applying, through the pair of electrodes during a recovery phase of the neural stimulation procedure, a second current to the bundle of nerve fibers, the first current and the second current having opposite polarities;
    determining sampled voltages between the pair of electrodes during the stimulation phase, during the recovery phase, or between the stimulation phase and the recovery phase;
    determining a charge buildup in the bundle of nerve fibers based on the sampled voltages, wherein determining the charge buildup includes routing samples of the voltages to a comparator device for identifying a positive charge buildup or a negative charge buildup based on a value of a voltage differential between the pair of electrodes, wherein the pair of electrodes are configured to be temporarily shorted together to allow the charge build up to dissipate;
    applying, through the pair of electrodes during the stimulation phase or during the recovery phase, a delta current to the bundle of nerves based on the sampled voltages to minimize the charge build up.

2. The method of claim 1, wherein applying the first current includes stimulating the bundle of nerve fibers at a frequency between 10 kilohertz and 50 kilohertz.

3. The method of claim 1, wherein applying the first current includes stimulating the bundle of nerve fibers at a frequency between 1 hertz and 10 kilohertz.

4. The method of claim 1, wherein applying the first current includes stimulating the bundle of nerve fibers at a frequency above 50 kilohertz.

5. The method of claim 1, wherein applying the first current includes activating a current source by actuating a pair of switches to transition from an open position to a closed position, wherein the pair of switches in the closed position define a flow path for the first current.

6. The method of claim 5, wherein applying the second current includes activating the current source by actuating a second pair of switches to transition from the open position to the closed position subsequent to the pair of switches transitioning from the closed position to the open position, wherein the second pair of switches in the closed position define a new flow path for the second current.

7. The method of claim 1, wherein the comparator comprises an op-amp circuit.

8. The method of claim 1, wherein applying the delta current includes:
routing a voltage output signal from a comparator device to a selection input of a multiplexer;
determining, by the multiplexer, a value corresponding to the voltage output signal; and
routing a first voltage or a second voltage to a switch of a stimulation circuit for actuating the switch to a closed position to activate a current source to apply the delta current.

9. The method of claim 8, wherein the first voltage has a first value for actuating the switch to transition to the closed position concurrently with a pair of switches to define a current path for the first current, and wherein the second voltage has a second value for actuating the switch to transition to the closed position concurrently with a second pair of switches to define a second current path for the second current.

10. A system comprising:
a circuit configured to:
apply, through a pair of electrodes electrically coupled to a bundle of nerve fibers during a stimulation phase of a neural stimulation procedure, a first current to the bundle of nerve fibers;
apply, through the pair of electrodes during a recovery phase of the neural stimulation procedure, a second current to the bundle of nerve fibers, the first current and the second current having opposite polarities;
determine sampled voltages between the pair of electrodes during the stimulation phase, during the recovery phase, or between the stimulation phase and the recovery phase;
determine a charge buildup in the bundle of nerve fibers based on the sampled voltages, wherein determining the charge buildup includes routing samples of the voltages to a comparator device for identifying a positive charge buildup or a negative charge buildup based on a value of a voltage differential between the pair of electrodes, wherein the pair of electrodes are configured to be temporarily shorted together to allow the charge build up to dissipate; and
apply, through the pair of electrodes during the stimulation phase or during the recovery phase, a delta current to the bundle of nerves based on the sampled voltages to minimize the charge build up.

11. The system of claim 10, wherein applying the first current includes stimulating the bundle of nerve fibers at a frequency between 10 kilohertz and 50 kilohertz.

12. The system of claim 10, wherein applying the first current includes stimulating the bundle of nerve fibers at a frequency between 1 hertz and 10 kilohertz.

13. The system of claim 10, wherein applying the first current includes stimulating the bundle of nerve fibers at a frequency above 50 kilohertz.

14. The system of claim 10, wherein applying the first current includes activating a current source by actuating a pair of switches to transition from an open position to a closed position, wherein the pair of switches in the closed position define a flow path for the first current.

15. The system of claim 14, wherein applying the second current includes activating the current source by actuating a second pair of switches to transition from the open position to the closed position subsequent to the pair of switches transitioning from the closed position to the open position, wherein the second pair of switches in the closed position define a new flow path for the second current.

16. The system of claim 10, wherein the comparator comprises an op-amp circuit.

\* \* \* \* \*